United States Patent [19]

Overfield

[11] Patent Number: 4,865,746
[45] Date of Patent: Sep. 12, 1989

[54] CHROMATOGRAPHIC ANALYSIS OF HYDROCARBONS

[75] Inventor: Robert E. Overfield, Calgary, Canada

[73] Assignee: Exxon Research and Engineering Company, Florham Park, N.J.

[21] Appl. No.: 143,744

[22] Filed: Jan. 14, 1988

Related U.S. Application Data

[63] Continuation-in-part of Ser. No. 6,382, Jan. 23, 1987.

[51] Int. Cl.$^4$ ............................................. B01D 15/08
[52] U.S. Cl. ............................. 210/656; 210/198.2; 73/61.1 C; 250/301; 250/373; 436/140; 436/143; 436/161
[58] Field of Search ............... 436/139, 140, 143, 161; 210/656, 659, 198.2; 73/61.1 C; 250/301, 373

[56] References Cited

U.S. PATENT DOCUMENTS

| | | | |
|---|---|---|---|
| 3,676,649 | 7/1972 | Burk | 73/61.1 C |
| 3,897,213 | 7/1975 | Stevens | 73/61.1 C |
| 3,975,727 | 8/1976 | Mader | 73/61.1 C |
| 4,199,323 | 4/1980 | Miller | 73/61.1 C |
| 4,254,656 | 3/1981 | Sanford | 73/61.1 C |
| 4,264,814 | 4/1981 | Freund | 250/373 |
| 4,265,634 | 5/1981 | Pohl | 73/61.1 C |
| 4,455,084 | 6/1984 | Webb | 73/61.1 C |
| 4,476,713 | 10/1984 | Alfredson | 73/61.1 C |
| 4,563,585 | 1/1986 | Ward | 250/373 |
| 4,567,753 | 2/1986 | Miller | 73/61.1 C |
| 4,614,871 | 9/1986 | Driscoll | 250/373 |
| 4,631,687 | 12/1986 | Kowalski | 73/61.1 C |
| 4,671,103 | 6/1987 | Dickakian | 73/61.1 C |
| 4,733,084 | 3/1988 | Oosaka | 250/373 |

OTHER PUBLICATIONS

Krstulovic, Selective Monitoring of Polynuclear Aromatic Hydrocarbons by High Pressure Liquid Chromatography with a Variable Wave Length Detector, Analytical Chemistry, vol. 48, No. 9, Aug. 1976, pp. 1383-1386.
Bullet et al., "Journal of Chromatography", vol. 206, pp. 289-300, 1981.
Hennion et al, "Journal of Chromatography", vol. 280, pp. 351-362, 1983.

*Primary Examiner*—Ernest G. Therkorn
*Attorney, Agent, or Firm*—Jay Simon

[57] ABSTRACT

A sample of a hdyrocarbon oil containing asphaltenes is chromatographically analyzed by forming a mixture of the oil with a weak solvent. The mixture is passed in contact with a column of a stationary phase of find solid particles of fully functionalized material, followed by a weak solvent. The solvent, after recovery from the column, is analyzed for aromatics by UV-absorption of UV radiation in the range 200 to 400 nm. The absorbance of the UV light by the irradiated eluents across the UV wavelength range is monitored and the integral of absorbance is derived as a function of photon energy across the wavelength range. The magnitude of the derived integral in at least one time interval corresponding with at least aromatics in the eluent from the stationary phase is measured as an indication of the level of aromatics in the oil sample. The weak solvent may be followed by a strong solvent which, in turn, may be followed by a strong solvent which is modified by the addition of a hydrogen bonding solvent.

7 Claims, 4 Drawing Sheets

NMR AROMATICITY COMPARISON DEMONSTRATES
ACCURACY OF AROMATIC CORE DETECTOR

PREDICTED AROMATICITY — 1.0 °AROMATIC CORES + 2.0°POLARS CORES

CHROMATOGRAM OF HEAVY ARABIAN VACUUM RESID

CHROMATOGRAPHIC ANALYSIS OF HYDROCARBONS

CROSS REFERENCE TO RELATED APPLICATIONS

This application is a continuation-in-part application of copending Serial No. 006,382, filed January 23, 1987.

FIELD OF THE DISCLOSURE

The present invention relates to a method of chromatographic analysis of a hydrocarbon oil, equipment therefor, and to a process for refining or upgrading a hydrocarbon feed employing said method of, and equipment for, chromatographic analysis The present invention relates in particular to a method to determine the level of components present in a hydrocarbon oil, especially aromatics.

Chromatography is a well-documented and widely used laboratory technique for separating and identifying the components of a fluid mixture, e.g. a solution, and relies on the different relative affinities of the components between a stationary phase and a mobile phase which contacts the stationary phase.

In a typical example of chromatography, the stationary phase is a suitable particulate solid material which is substantially uniformly packed into a tube so as to form a column of the stationary phase material. The mobile phase may be the fluid under investigation, or more commonly, a solution of the fluid under investigation. The solvent used in the solution is usually first passed through the column of solid stationary phase and thereafter a small sample comprising a solution of the fluid under investigation is passed through the column, followed by solvent alone. The components of the fluid will have different affinities for the stationary phase and will therefore be retained at different regions along the length of the column for different times For some components, the affinity will be so slight that virtually no retention is evident while for others, the affinity might be so great that the components are not recovered from the column even after considerable periods of time have elapsed since they were introduced into the column and subjected to the potential eluting properties of the solvent.

BACKGROUND OF THE INVENTION

Chromatography has been employed as a means of analyzing mixtures of hydrocarbons and other compounds found in petroleum oil.

In Petroanalysis 81, Chapter 9, it is disclosed that a hydrocarbon mixture combined with a solvent results in an eluate being recovered from the exit end of a chromatographic column which comprises the following types of molecular species, in order, namely: saturates (e.g. paraffins and naphthenes), olefins and aromatics. The remaining molecular species, which are (in general) polar compounds, have a relatively high affinity for the solid chromatographic material and can only be recovered in a reasonable time and reasonably completely by interrupting the flow of the solvent and substituting therefor a different solvent having a relatively high affinity for, e.g., heteroaromatic compounds. The said different solvent is passed through the column in a direction which is opposite to that of the first solvent so that after a reasonable time interval of this so-called back-flush, polar compounds (resins) are present in the back-flush eluate. The change in solvent from the first solvent, pentane, to the second solvent, methyl t-butylether, necessitates the use of two different eluent detectors, i.e. one using refractive index and the other using ultra-violet absorbance at 300 nm.

Backflushing is inconvenient because of the mechanical complications involved in automating a chromatography unit utilizing it and also because it, in itself, does not ensure complete recovery of chemical species which are strongly adsorbed by the stationary phase of the column.

In Journal of Liquid Chromatography, 3(2), 229–242 (1980), a hydrocarbon mixture containing asphaltenes is subjected to chromatographic analysis only after mixing the mixture with hexane to precipitate asphaltenes which are separated by filtration and then determined gravimetrically. The hexane solution of the remaining hydrocarbons is then passed through a column of particles of u-Bondapak-$NH_2$ where it separates into an eluent comprising, initially, saturates and then aromatics, as determined by the refractive index of the eluent. Resin which is retained on the column is backflushed off the column and determined by difference. The separation quality of the column is maintained by flushing it with a solution of 1/1 methylene chloride/acetone after every 20 samples and then regenerating with methylene chloride and hexane for repeatable retention times. Changes in the refractive index of the eluents, indicative of the presence of respective chemical species, are monitored and correlated with absolute amounts of the chemical species by means of a Hewlett-Packard 3354B computer using the so-called "Zero" type method The drawbacks of this technique are that: (1) asphaltenes are determined gravimetrically rather than by chromatography so that the technique does not lend itself readily to automatic operation; (2) backflushing is employed, and not all the material in the sample fed to the column is recovered in the eluent as is evidenced by the stated need to clean the column periodically (further reference to this significant problem will be made hereinafter); (3) the refractive index detector which is employed has a response which varies with each type of molecular group such as paraffins, naphthenes, aromatics and resins, and therefore cannot provide a universal response for a given mass which is independent of the nature of the sample of the feedstock which is being analyzed.

In Journal of Chromatography, 206 (1981) 289–300, Bollet et al., a rapid high-performance liquid chromatography technique for separating heavy petroleum products into saturated, aromatic and polar compounds is described. A column containing a stationary phase of silica bonded $NH_2$ ("Lichrosorb $NH_2$") is used. Two chromatographic analyses are needed in order to determine the composition of a sample. In the first analysis, saturated compounds are separated from aromatic and polar compounds, using hexane or cyclohexane as the mobile phase. In the second analysis, saturated and aromatic compounds are separated from polar compounds using 85 vol % cyclohexane, 15 vol % chloroform as the mobile phase. The eluents are monitored by differential refractometry for saturated, aromatic and polar compounds, and by ultraviolet photometry for polar compounds. The proportions of saturated and polar compounds are said to be determinable by these monitoring techniques and the proportion of aromatic compounds found by difference. However, the method described, in common with all other reports of high performance liquid chromatography (HPLC) for analysis of samples of heavy hydrocarbon oil mixtures, is limited by the lack of a means and method for quantitative and feedstock-independent detection and monitoring. Thus, for both refractive index (RI) and ultraviolet (UV) detectors, "response factors" must be derived by separating samples of the feedstock on a larger scale, known in the art as "semi-preparative liquid chromatography" and then gravimetrically weighing the recovered analyte (after removal of the solvent(s) added to the sample for the purpose of the chromatographic separation). Response factors are dependent on the nature of the feedstock and its boiling range, and it is therefore essential to perform the relatively large-scale separation to obtain accurate results with the HPLC analysis. Thus, the potential benefits of speed and increased resolution which should be possible with HPLC have not heretofore been fully realized in practice. The technique of Bollet et al is compared with the method of the invention in the Comparative Example given hereinafter.

Reference is also made to Klevens and Platt, J. Chem. Phys. 17:470 (1949). Similarities are reported in the total oscillator strength for-electronic transitions of cata-condensed aromatics. However, the article does not relate to HPLC analysis, nor does it recognize or suggest that a UV detector operating in a specific wavelength range can be used in HPLC to derive an integrated oscillator strength output which quantifies the aromatic carbon in petroleum and shale oil feedstocks. Furthermore, cata-condensed aromatics constitute only a minor fraction of the various aromatics in a hydrocarbon feedstock such as petroleum. Other aromatics, including para-condensed aromatics, alkyl aromatics, and thiophenic aromatics which behave spectroscopically differently from cata-condensed aromatics, are also generally present in a hydrocarbon feedstock.

SUMMARY OF THE INVENTION

It is an object of the present invention to provide a simpler, more comprehensive and more accurate method of, and equipment for, analyzing mixtures of compounds (particularly, but not exclusively, mixtures of hydrocarbons) by liquid chromatography.

It is an object of the invention to provide a process for refining and/or upgrading hydrocarbons using novel chromatographic method and equipment to regulate and/or optimize said process.

It is a further objective of the invention to solve the problem of how to quantify aromatics in hydrocarbon oil.

It is another objective of the present invention to quantify not only the aromatics but also the saturates and polars in the hydrocarbon oil and, further, to use this information, along with the qualitative levels of aromatics, to determine the extent of saturated substitution of aromatic and polar components of hydrocarbon oils. According to the present invention from one aspect there is provided a method for the chromatographic analysis of hydrocarbon oil, comprising the steps of:

(a) passing a mixture of the hydrocarbon oil and a carrier phase in contact with a chromatographic stationary phase over a first time interval so as to retain components of said hydrocarbon oil on said stationary phase;

(b) passing a mobile phase in contact with said stationary phase after step (a) over a second time interval, for eluting different retained components of said oil from said stationary phase at different time intervals, and recovering the mobile phase which has contacted the stationary phase together with the components eluted from the stationary phase;

(c) irradiating the recovered mobile phase with UV light having a wavelength range of which at least a part is within about 200 nm to about 400 nm over a sufficient time period that the recovered components in the recovered mobile phase are subjected to said irradiation, said mobile phase being substantially transparent to UV light within said wavelength range;

(d) monitoring the absorbance of said UV light by said irradiated components across said wavelength range and deriving the integral of absorbance as a function of photon energy across said wavelength range; and (e) measuring the magnitude of said derived integral in at least one selected time interval corresponding with the elution of one or more components.

The mobile phase and the carrier phase can be liquids or gases or supercritical fluids. Usually they will be liquids.

In a preferred way of performing the invention the recovered mobile phase from the stationary phase is irradiated with UV light having a wavelength range within the range 230 to 400 nm. A scaling factor of 2 is applied to the derivation of the integral of absorbance so that the magnitude of said derived integral of absorbance is doubled, and said magnitude is measured in step (e) in a time interval corresponding with polar components in said mobile phase recovered from the stationary phase.

In a preferred way of putting the invention into effect, the absorbance of said UV light by said irradiated components is monitored using a diode array detector.

The present invention is also concerned with calibration so as to determine the different ring-numbers of aromatics present in the hydrocarbon oil. Calibration is achieved essentially by testing a sample of hydrocarbon oil according to the method as disclosed herein having known aromatic rings present, so as to associate the different times at which the different aromatics elute from the stationary phase with the ring-numbers of those different aromatics. This technique is described in more detail below.

According to the invention from another aspect there is provided a process for refining or upgrading a petroleum hydrocarbon feed, in which samples of hydrocarbon oil produced in the process are each chromatographically analyzed by a method as defined above to determine the level present of at least one component in the oil, and in which the operation of the process is controlled in dependence upon the determined level present of said at least one component.

Usually but not necessarily the control of the operation of the process is such as to oppose any rise in value of the level present of said at least one component above a predetermined value.

One preferred way of performing the present invention provides a method of chromatographic analysis of a hydrocarbon oil, which may or may not contain asphaltenes, comprising the steps of:

(a) forming a mixture of a sample of the oil with a weak solvent having a solubility parameter in the range of from 7.6 to 8.8 $cal.^{0.5} cm^{-1.5}$;

(b) passing the said mixture in contact with a solid chromatographic stationary phase selected from:
   (i) a solid chromatographic stationary phase having surface hydroxyl groups of which substantially all have been substantially fully functionalized by at least one functionalizing group selected from at least the following functionalizing groups —$NH_2$, —CN, —$NO_2$, a charge-transfer adsorbent, a charge-transfer adsorbent functionalized with trinitroanilinopropane or tetranitrofluorenone, a homologue of any one of the foregoing and a combination of two or more of the forgoing;
   (ii) a solid chromatographic stationary phase having a coronene capacity factor, with a mobile phase comprising cyclohexane and 0.03 vol % isopropanol, not exceeding 5.0 (preferably 2.5 or less); and
   (iii) a solid chromatographic phase comprising a combination of features of (i) and (ii);
(c) passing in contact with the said solid chromatographic stationary phase a weak solvent (preferably cyclohexane) having a solubility parameter in the range of from 7.6 to 8.8 $cal^{0.5} cm^{-1.5}$ for a first time period at least during and after step (b) and recovering the weak solvent which has contacted the solid stationary phase;
(d) monitoring the weak solvent recovered in step (c) for a second time period comprising at least a time interval after the first time period to detect eluent comprising any aromatic hydrocarbons;
(e) monitoring the weak solvent recovered in step (c) to detect eluent comprising any saturated hydrocarbons simultaneously with step (d) and after step (d);
(f) passing in contact with the said solid chromatographic stationary phase a strong solvent having a solubility parameter in the range of from 8.9 to 10.0 for a third time period which is at least after the second time period and recovering strong solvent which has contacted the said stationary phase;
(g) monitoring the strong solvent recovered in step (f) to detect eluent comprising any heteroaromatic compounds, polar compounds and asphaltenic materials;
(h) passing in contact with the said solid chromatographic stationary phase for a fourth time period which is at least after the third time period a strong solvent modified with a hydrogen-bonding solvent (such as an alcohol) which is miscible with the strong solvent, and recovering strong modified solvent which has contacted the said stationary phase; and
(i) monitoring the recovered strong modified solvent recovered in step (h) to detect any eluent comprising moieties selected from at least one of the group consisting of polar compounds and asphaltenic materials.

Preferably, the change from weak solvent to strong solvent is effected over a finite period of time, i.e. there is a progressive change in solvent rather than a step change It is found that superior separation is achieved in this way.

With reference to step (h), the strongly polar solvent and/or hydrogen-bonding solvent preferably has the following properties: (i) It must be capable of dissolving polar compounds and asphaltenes of the types found or anticipated in the sample. As a rule of thumb, a solvent or combination of solvents having a polarity between those of toluene and carbon disulfide will satisfy this requirement, and dichloromethane is a convenient and preferred solvent meeting this criterion. (ii) It must be capable of displacing the most polar heavy oil molecules from the solid adsorbent material. The addition to the solvent of one or more alcohols miscible therewith provides this property, and when the solvent is based on dichloromethane, a convenient and preferred alcohol is isopropanol in volume concentrations in the range of from 1 to 50%, e.g. 10 vol % or thereabouts. (iii) If ultraviolet spectroscopic analysis is employed for mass detection, as explained herein, the solvent (or combination solvent) must be transparent to UV radiation in the wavelength range employed (iv) If a mass detection step is used (e.g., gravimetric, flame ionization, inter alia) in which the removal of the solvent is necessary, the solvent must be relatively volatile for easy separation of solvent-free eluent, and the solvent must not associate too strongly with polar molecules in the eluent.

Preferably, step (j) is effected after step (i) by passing a weak solvent in said one direction in contact with the said stationary phase for a fifth time period which is at least after the fourth time period, said weak solvent preferably being the same as, or fully miscible with, the weak solvent of step (c). Preferably after step (j), steps (a) to (j) are repeated as described herein using another oil sample in step (a).

The monitoring for eluents in steps (e), (g) and (i) is effected by UV absorption employing UV of selected wavelength(s), the solvents used in steps (a), (c), (f) and (h) preferably being transparent to UV of the selected wavelength(s). A highly significant benefit of employing UV absorption to monitor the eluents is that it can be employed for the accurate determination of the mass of aromatic carbon therein, as described hereinbelow.

Aromatic compounds of differing ring numbers and substitution show differing ultraviolet absorbance spectra. It is therefore not possible to choose a single wavelength to determine all of them. Each aromatic type has a different intrinsic absorbance per unit molar concentration (the extinction coefficient) at any given wavelength, and in a complex mixture it is not possible to assign a constant response factor which will relate the absorbance to the mass eluting from the column. To overcome this limitation, a preferred way of performing the invention has been devised. The new method utilizes full UV absorbance spectra in the region 200 to 400 nm. Spectra can be taken rapidly on the oil components eluting from a chromatography column with a diode array detector. There have been published examples of these detectors in oil analysis (e.g., by K.W. Jost et al in Erdol und Kohle-Erdgas - Petrochemie 37(4):178(1984)), but no reports of the quantitative measurement of aromatic carbon from UV spectra. It has been discovered by the present inventor that a mathematically derived quantity, termed the integrated oscillator strength (Q), calculated from the full absorbance spectrum is directly proportional to the level of aromatic carbon. The quantity Q is defined as:

$$= \int A(\epsilon) d(\epsilon) \qquad (1)$$

Where:
 A = absorbance
 $\epsilon$ = photon energy
 and the integral is taken over the region from 200 to 400 nm.

To derive the mass of aromatic carbon eluting from the column in any time period which defines an oil component, the quantity Q is simply integrated over that time period and then multiplied by an appropriate constant which reflects the light path length, integration time, etc.

One way in which Q can be determined will now be described, in the case of a diode array detector. Each detector produces an output signal proportional to the intensity, I, of the light it detects. A computer converts each detector output to a quantity $A(\lambda)$ — i.e. absorbance, where $\lambda$ represents wavelength — where $A = -\log_{10}(I/I_o)$, $I_o$ being the intensity of the UV source. The bandwidth $\Delta\lambda$, received by each individual detector in the detector array, is the same (e.g. 2 nm) but the wavelength varies (by an increment or decrement equal to the bandwidth) from each detector to the next. Therefore, the computer multiplies the quantity $A(\lambda)$ by a weighting factor $$E(\lambda) = hc\left[\frac{1}{\lambda - 0.5(\Delta\lambda)} - \frac{1}{\lambda + 0.5(\Delta\lambda)}\right],$$

and sums across the UV spectrum to derive the integrated oscillator strength Q.

The validity and accuracy of this approach has been established by comparison to model components which have been injected at known weights into the chromatography system. Some examples are given in Table I.

TABLE I

OSCILLATOR STRENGTH QUANTIFIES AROMATIC CORES WITH FULL UV SPECTRA

| CLASS | COMPOUND | STRUCTURE | OSCILLATOR STRENGTH MOLE AROMATIC CARBON |
|---|---|---|---|
| 1 RING | TOLUENE | 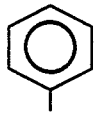 | 151* |
| 2 RING | NAPHTHALENE | 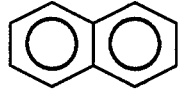 | 853 |
|  | 2 ETHYLNAPHTHALENE |  | 1041 |
| 3 RING | ANTHRACENE | 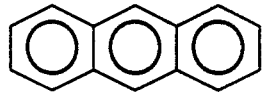 | 901 |
|  | PHENANTHRENE | 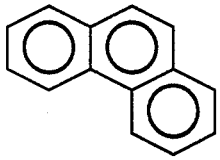 | 810 |
|  | 1 METHYLPHENANTHRENE | 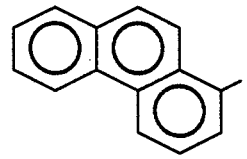 | 918 |
| 4 RING | 1, 2, BENZANTHRACENE | 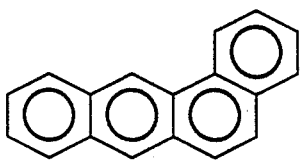 | 995 |
|  | PYRENE | 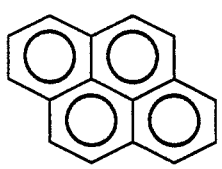 | 827 |

TABLE I-continued
OSCILLATOR STRENGTH QUANTIFIES AROMATIC CORES WITH FULL UV SPECTRA

| CLASS | COMPOUND | STRUCTURE | OSCILLATOR STRENGTH MOLE AROMATIC CARBON |
|---|---|---|---|
| | TRIPHENYLENE | | 791 |
| | FLUORANTIRENE | | 971 |
| POLARS | 1, 2, 5, 6 DIBENZANTHRACENE | 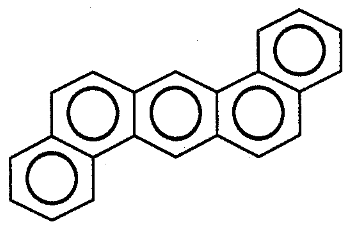 | 545** |
| | CARBAZOL | | 393** |
| | PHENANTHRIDINE | | 486** |

*ONE RING AROMATICS NOT QUANTIFIED DUE TO SOLVENT CUT-OFF
**POLARS OSCILLATOR STRENGTH MEASURED 234–400 nm ONLY

The measured integrated oscillator strength (Q) on polar compounds is multiplied by a factor of about 2.0 (or the integrated oscillator strength is multiplied by a factor of about 2.0 before it is measured) to derive the aromatic carbon because a part of the spectral region cannot be measured due to solvent (e.g., dichloromethane) absorbance. The accuracy of the integrated oscillator strength method or technique has also been demonstrated on whole oils by comparison to the determination of aromatic carbon by Nuclear Magnetic Resonance (NMR) in various oil samples, as shown in FIG. 1 of the drawings wherein the abscissa gives the 13C-NMR results in units of weight percent aromatic carbon and the ordinate gives the predicted values in the same units, the predicted values having been derived from the integral of A ($\epsilon$) d $\epsilon$. The straight-line graph illustrating the linear correlation of the NMR values and the integrated oscillator strength values represents parity The data fits the parity line even for oils of very different degree of saturated substitution, such as vacuum gas oils and coker gas oils, and oils of very different polar content, such as hydrotreated gas oils and vacuum residua The theoretical basis for the independence of this quantity to aromatic type is not completely understood.

The total mass of components eluting from the column may be determined by, for example, differential refractometry, solvent evaporation followed by flame ionization of the oil, or solvent evaporation followed by light scattering off the remaining oil droplets. There are commercially available detectors for each of these procedures. Differential refractometry has the drawbacks that the refractive index of a component varies with its aromaticity and with the degree to which the saturated carbon is paraffinic or naphthenic. These drawbacks lead to the need to use feedstock-type-dependent response factors to relate the measured refractive index to the mass of component eluting Accordingly, it is preferred, according to a preferred way of performing the invention, to use solvent evaporation followed by either flame ionization or light scattering to measure the total mass of oil components independently of the feedstock composition or the feedstock type. In the case of flame ionization, the particular instrument used (the flame ionization equipment described by J.B. Dixon of Tracor Instruments in paper No. 43 at the 1983 Pittsburgh Conference on Analytical Chemistry) has been found to cause some volatilization of lower boiling range oils along with the solvent evaporation, so it was most useful with vacuum distillation residua. In the case of light scattering, it is recognized that the light scattering response is a complicated function of the mass of solute eluting, and an appropriate calibration function must be derived A recent publication (T.H. Mourey and L.E. Oppenheimer, Analytical Chemistry, 56: 2427–2434(1984)) addresses the use of a light scattering detector for HPLC of polymers. It has been demonstrated by the inventor of the present invention that for oil systems, this detector may be used to measure total component masses independently of feedstock type. The calibration functions are:

$$\text{Mass} = K_1 * (\text{response})^x \quad (2)$$

where $x \leq 1$ at low response intensities; and $$\text{Mass} = K_2 * (\text{response})^x \quad (3)$$

where $y \geq 1$ at high response intensities.
$K_1$ and $K_2$ are constants

The combination of using one detector to measure aromatic carbon mass and another to measure total mass allows the saturated carbon substitution to be determined by difference or ratio). It is believed that this is a totally new concept in HPLC. Its validity has been established by comparisons of HPLC to mass spectroscopic analyses and by showing that the aromaticity of individual aromatic and polar components increases as expected during thermal treatment.

The invention, according to a preferred application, provides a method of evaluating the quality of a hydrocarbon mixture comprising analyzing at least one sample of the hydrocarbon mixture by the method as herein described and thereby determining the proportions of species selected from at least one of the following: saturates, aromatics, polynucleararomatics, polar compounds, asphaltenes and a mixture comprising at least two of the foregoing. The hydrocarbon mixture may be a feedstock for a refining process or an intermediate processed oil between two refining steps. The evaluation performed by this preferred method of the invention enables the refining process or processes to be adjusted as necessary (within their permissible operating limits) to produce a product and/or intermediate product having a composition which matches or closely approximates to the optimum specification for the product and/or intermediate product.

The invention, in one application, also provides a process for refining or upgrading a petroleum hydrocarbon feed containing asphaltenic materials in which the feed is passed to a fractionation unit having a temperature and pressure gradient thereacross for separation into components according to the boiling ranges thereof, said components being recovered from respective regions of the fractionation unit and including a gas oil component boiling in a gas oil boiling range which is recovered from a gas oil recovery region of the unit, wherein discrete samples of gas oil fraction are taken from the recovered gas oil fraction at intervals and each analyzed by the method as herein described, and wherein a signal representative of the amount of asphaltenic material present in each sample is generated and employed to modulate the operation of the fractionation unit so that the amount of polar component in the gas oil component is maintained below a predetermined amount.

The invention, in another application, further provides a process for refining or upgrading a petroleum hydrocarbon feed (e.g., boiling in the gas oil boiling range) in which the feed is passed to a catalytic cracking unit and converted to cracked products including upgraded hydrocarbon materials, wherein discrete samples of the feed passing to the catalytic cracking unit are taken at intervals and each analyzed by the method as described herein, and a signal representative of the amounts of polar components and aromatic components having at least three rings ("3+ring aromatics") is generated, and the feed is either blended with a higher quality feed or subjected to a catalytic hydrogenation treatment or both blended and catalytically hydrogenated if and/or when said signal corresponds to amounts of 3+ring aromatic components and polar components in excess of predetermined amounts, the amount of blending and/or the intensity of said catalytic hydrogenation treatment being increased and decreased with respective increases and decreases in the magnitude of the said signal.

The invention, in yet another application, also provides a process for refining and upgrading a petroleum hydrocarbon feed containing undesirable contaminating components selected from asphaltenic materials, aromatic components containing at least three conjugated aromatic rings ("3+aromatics"), polar components and mixtures of at least two of said contaminating components comprising the steps of mixing a stream of the hydrocarbon feed with a stream of a selective refining agent at selected refining conditions and separately recovering from the resulting mixture (i) a hydrocarbon raffinate stream having a reduced content of polar components and aromatic components; and (ii) a stream of a mixture containing solvent and at least one of said contaminating components, wherein discrete samples of the raffinate stream are taken at intervals and each analyzed by the method as herein described and wherein a signal representative of the amount of contaminating component is derived, the signal being employed directly or indirectly to vary or regulate the said refining conditions so as to maintain the amount of contaminating component in the raffinate below a selected amount.

DESCRIPTION OF THE DRAWINGS

The invention is now further described by way of example with reference to the drawings in which.

DETAILED DESCRIPTION OF THE INVENTION

In the particular description herein, only those features which have a direct bearing on the disclosed embodiments of the invention will be mentioned; features which will be well-known to those skilled in the art will not be referred to.

Figure 1:
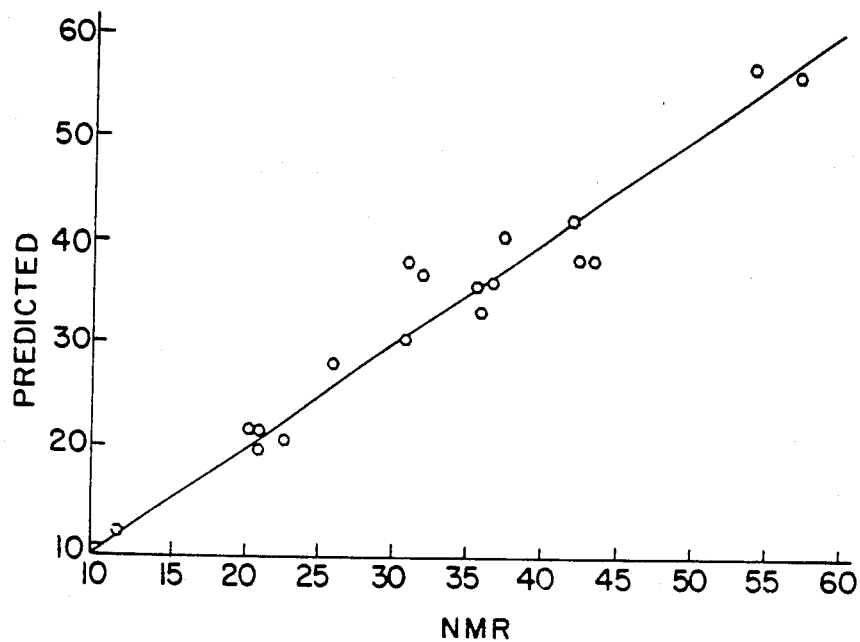
FIG. 1 is a regression-analysis graph of the weight percent of aromatic carbon in various hydrocarbon oil samples by NMR (on the abscissa) versus the predicted total aromatic carbon weight percent in the eluent as derived from the integrated oscillator strength.

FIG. 1 was obtained by NM determinations and integrated oscillator strengths I on samples of 6 virgin gas oils (VGO), 1 heavy coker gas oil (HKGO), 3 deasphalted oils (DAO), 5 heavy Arabian vacuum residua (HAVR) fractions and 4 vacuum residua, and the predicted aromaticities were obtained from the integrated oscillator strengths. The measured polar aromatic cores were multiplied by a factor of 2.0. It is evident that this approach to UV detection provides a quantitative measurement of aromatics which is independent of feedstock type. The need for response factors is thus eliminated.

Figure 2:
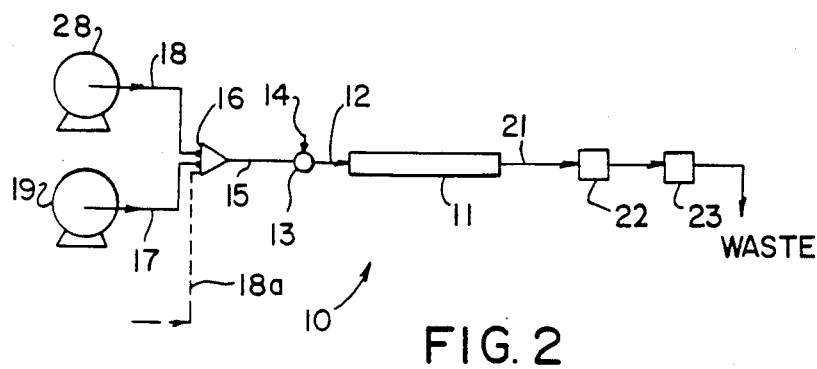
FIG. 2 is a schematic diagram showing one form of apparatus for use according to one way of performing the method of the invention.

Referring now to FIG. 2, the apparatus 10 comprises a chromatographic column 11 having an internal diameter of 4.6 mm and an overall length of 25 cm. The column 11 is packed by the well-known slurry method with a commercially available stationary phase consisting of substantially fully $NH_2$-functionalized silica in finely divided form, having a mean particle size in the range suitable for high performance liquid chromatography (HPLC), e.g. 5 to 10 $\mu$m.

A conduit 12 extends from the upstream end of the column to a sample injection valve 13, and samples are injected into the valve 13 and conduit 12 from a sample injection line 14.

A solvent pipe 15 extends from the upstream end of the valve 13 to the downstream end of a solvent mixing chamber 16 which is connected to two solvent tubes 17, 18 to receive different solvents from respective suitable pumps 19, 20. The operations of the pumps 19, 20 are regulated by microprocessors (not shown). Each pump 19, 20 is connected to receive a respective solvent from a source thereof (not shown). A third pump may optionally be added or a single pump with proportioning inlet valves to different solvent reservoirs may be employed.

At the downstream end of the column 11, a conduit 21 conducts solvent(s) and eluents from the column to a variable wavelength ultra-violet detector 22 and thencefrom to a mass-sensitive or mass-responsive detector 23 and thereafter to a sample disposal point and/or recovery and/or separation unit (not shown). The mass-sensitive or mass-responsive detector 23 may be a detector which monitors, or produces a signal in response to refractive index, flame ionization or light-scattering (after evaporation of solvent from the sample).

During the analysis, the microprocessor controllers regulate operation of the two pumps 19, 20 to maintain a substantially constant flow rate through column 11 of from 0.5 to 2.0 ml per minute. Initially, a weak solvent is employed which is substantially transparent to UV radiation and has a sufficient solubility parameter to dissolve all components of the sample to be introduced into the column but of which the solubility parameter is not so high that relatively sharp discrimination between different chemical types in the sample by HPLC will not be possible. The solubility parameter, delta, is the square root of the quotient of the energy of vaporization divided by its molecular volume (see C.A. Hansen et al., Encyclopedia of Chemical Technology by Kirk and Othmer, 2nd edition, Supplement, pages 889 to 910); i.e. delta $(E_v/V_m)0.5$. The solubility parameter of the weak solvent should be in the range of from 7.6 to 8.8 cal.$^{0.5}$cm$^{-1.5}$ and a preferred weak solvent is cyclohexane which dissolves all hydrocarbon components of hydrocarbon oil samples without causing precipitation of asphaltenes. Other weak solvents which may be used in place of cyclohexane are nonane, decane, dodecane, hexadecane, eicosane and methylcyclohexane, and combinations of at least two of the foregoing. Preferably, the solvent used is cyclohexane containing a trace proportion of a polar solvent in order to maintain the adsorption properties of the stationary phase at a constant value by deactivating any residual silanol groups on the stationary phase. The preferred polar solvent for this purpose is an alcohol, particularly 2-propanol, and preferably a mixture of 99.99 volumes cyclohexane and 0.01 volumes 2-propanol is pumped by pump 19 to the column 11 during a first time period of operation.

During the first time period of operation, a sample of the hydrocarbon which is to be analyzed is passed via line 14 into injector valve 13 at a datum time where it co-mingles with the weak solvent from pump 19 to form a substantially uniform solution which is free of precipitated material such as asphaltenes. The magnitude of the sample is not critical within the limits which are conventional for high performance liquid chromatography, and a sample of 0.4 mg is usually satisfactory. The resulting solution passes into the upstream end of the column 11. In an alternative embodiment, a sample comprising a solution of the hydrocarbon in which the solvent is a weak solvent (conveniently but not necessarily the same solvent as is delivered by the pump 19) is introduced through injector valve 13 as a "slug" which is propelled through the column by further weak solvent from pump 19.

The liquid which emerges from the downstream end of the column 11 is constantly monitored in UV detector 22 and mass-sensitive detector 23. The UV-monitoring detector 22 and mass-sensitive detector 23 operate by the principles described herein. The response of these detectors may be digitized and automatically converted into levels or proportions of the various components in the oil sample.

The response in the mass-sensitive detector will typically start before the absorption of UV is detected due to the lower retentivity of saturated hydrocarbons than aromatics by the stationary packing material in the column 11 and will tend to overlap in time the UV absorption period as some aromatic hydrocarbon molecules pass through the UV detector at the same time as more diffusive aromatic molecules are passing through the mass-sensitive detector.

The diffusivity or rate of elution of molecules containing aromatic rings, as manifested by their rate of passage through the column 11, depends to a major extent on the number of aromatic rings in the molecules. Molecules having a single aromatic ring are eluted relatively rapidly while molecule containing two or more aromatic rings are eluted more slowly. Thus, by calibrating the column 11 with molecules containing different numbers of aromatic rings, it is possible to characterize eluted molecules in accordance with the time they have taken to pass through the column 11. Calibration is suitably effected with, e.g. toluene (one aromatic ring), anthracene (three condensed aromatic rings) and coronene (six condensed aromatic rings). The calibration may be effected with additional multi-ring compounds and/or different multi-ring compounds.

During operation of the method as disclosed herein, substantially all single-aromatic molecules will elute within a time span comparable with that of toluene, three-ring molecules will elute within a time span comparable with that of anthracene after the time span of the single-aromatic molecules, and six-aromatic ring compounds will elute after the time span of anthracene during a time span comparable with that of coronene. Molecules having numbers of aromatic rings between those of toluene and anthracene and between anthracene and coronene will elute after time periods between the respective pairs of molecules used for the calibration.

When substantially all the saturated and aromatic hydrocarbon molecules have been eluted from the column 11 by the weak solvent, as evidenced by a decline in the UV absorption and refractive index to virtually their base values with the solvent only, a strong solvent (i.e. a solvent having relatively high polarity) is passed into the column by pump 20 at a progressively increasing rate while the weak solvent is pumped by pump 19 at a corresponding progressively reducing rate so that the total volume-rate of solvent is substantially unaltered. After a selected third time period, the weak solvent is totally absent and the only solvent passing to the upstream end of the column 11 is the strong solvent. The strong solvent has a solubility parameter in the range of from 8.9 to 10.0 cal$^{0.5}$·cm$^{-1.5}$ and is transparent to UV. A suitable strong solvent must be transparent to UV radiation at as low a wavelength as possible to facilitate calculation of the oscillator strength. The strong solvent must have a polarity between those of toluene and carbon disulfide, and is suitably dichloromethane. The dichloromethane may contain an alcohol in order to enhance its ability to elute polar high molecular weight molecules. Suitably, the alcohol is 2-propanol, and the strong solvent may consist of 90 vol% dichloromethane and 10 vol% 2-propanol. In a modification of the apparatus of FIG. 2 as so far described, pumps 19 and 20 may be employed respectively for passing the weak and strong solvents (e.g., cyclohexane and dichloromethane) via respective tubes 17 and 18 into the mixing chamber 16, and there may be an additional tube 18a for conducting the alcohol or other high polarity eluting material from a respective third pump (not shown) to the mixing chamber 16. The third pump is preferably microprocessor controlled in relation to pumps 19 and 20 according to a predetermined sequence or program in a manner which is known in the art.

If the alcohol or other highly polar solvent modifier has not been introduced with the strong solvent in the third time period, it is introduced over a fourth time period (e.g. of five minutes or thereabouts). In either case, the alcohol or other highly polar solvent modifier is introduced in steadily increasing rate with a correspondingly reducing rate for the strong solvent.

The modified strong solvent only is passed into the column 11 for a fifth time period to elute highly polar molecules from the column. The elution of polar molecules is detected by both detectors. The polar molecules of a typical hydrocarbon sample which contains asphaltenes are virtually completely eluted within a fifth time period of about 10 minutes, according to the relatively rapid decline in UV absorption after 3 to 10 minutes from the time when strong modified solvent only is pumped into the column.

When the elution of polar molecules is substantially completed, the strong solvent is progressively replaced by the weak solvent (i.e. 99.99 vol% cyclohexane with 0.01 vol% 2-propanol) over a sixth time period. Suitably, the sixth time period can be in the range from 1 to 10 minutes.

The weak solvent may be replaced by first interrupting the addition of the alcohol modifier to the strong solvent and then by progressively replacing the strong solvent by the weak solvent. The next hydrocarbon sample may then be passed into the column from injector valve 13 with weak solvent.

Figure 3A:
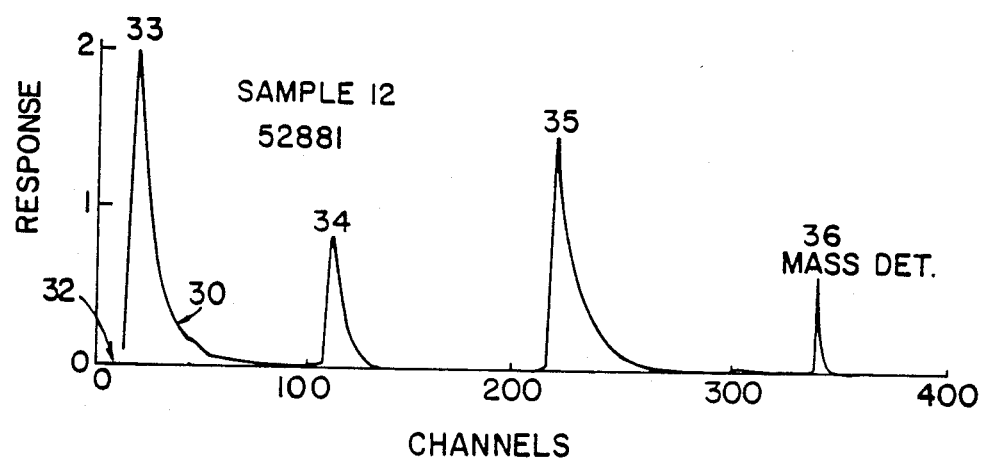
FIGS. 3a and 3b is a graph showing compositional data on the ordinate versus time on the abscissa for an analysis carried out using the apparatus of FIG. 2.
Figure 3B:
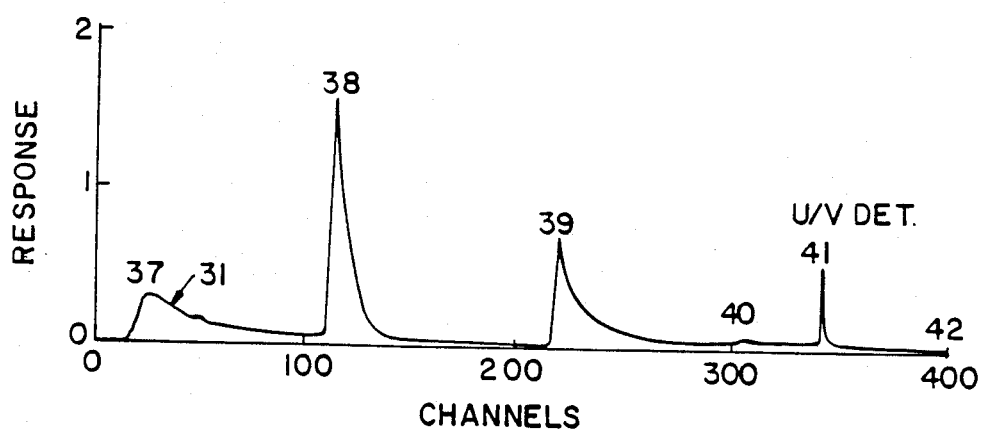

Reference is now made to FIG. 3 of the drawings in which the upper graph (3a) 30 shows the variation with time of the response of the material passing through the mass-sensitive evaporative light-scattering detector 23; and the lower graph (3b) 31 shows the variation with time of the UV oscillator strength of the material passing through the UV detector 22.

On the abscissa, the time is given in 3-second intervals or increments (hereinafter termed "channels" from time to time) from a datum time '0' which is 40 channels after the sample is injected.

The sample was 0.4 mg of heavy Arab vacuum residuum. The solvents were pumped by pumps 19, 20 either together in progressively changing proportions or individually to provide a constant solvent flow rate through the column 11 of 1.0 ml per minute.

In the initial time interval preceding the datum time, weak solvent only was passed from the pump 19 at the aforesaid rate of 1.0 ml/minute, and the light-scattering signal and UV oscillator strength were at constant levels during this time interval. The weak solvent alone was delivered by pump 19 through injector valve 13 for 7 minutes, from the time of injection of the hydrocarbon oil sample. Immediately thereafter, the strong solvent was progressively substituted for the weak solvent at a uniform rate (i.e. linearly over a period of 2 minutes). The strong solvent alone was then delivered by pump 19 through injector valve 20 for a period of 4.0 minutes, at which time it was progressively replaced over a period of 0.1 minutes by the modified strong solvent whose flow was thereafter maintained for a period of 12.9 minutes. In each case, a time lag arises, from the time of passing through the injection valve 13, for the sample or each solvent to reach the column and pass through it.

At the datum time, −40 channels, the 0.4 mg sample of vacuum residuum was injected from sample injection line 14 into injection valve 13. Due to the time lag, for the first 40 channels thereafter neither detector showed any deviation from the steady baseline before sample injection. After 11 channels later, the light-scattering signal as detected by detector 23 showed changes which comprised a sharp increase in response from the baseline 32 to a maximum point (point 33) followed by a progressive decrease towards the solvent-only value, interrupted at intervals by one or more increases in response. The light-scattering signal responded to the elution of 40 microgram of benz(alpha)anthracene which was included as an internal standard, and indicated by peak 34. The elution of polar heteroaromatic species due to a solvent change to dichloromethane was indicated by peak 35, and the elution of strongly polar heteroaromatic species due to a change in solvent to 90% dichloromethane, 10% isopropanol was indicated by peak 36.

With reference to the UV oscillator strength graph 31, it will be observed that an increase in absorbance from the baseline began at about 15 channels and attained a peak (point 37) at about 24 channels. The peak value of absorbance was maintained for a short time and thereafter maintained a height above the baseline indicative of the aromatics eluting at each particular time. At point 38, the response of the internal standard is apparent. At 219 channels, corresponding approximately with the time of complete substitution of strong solvent for weak solvent in the column, there was a steep rise in UV absorbance which rose to a peak (point 39) due to polar compounds and thereafter exhibited a relatively rapid decline. The small additional peak 40 represents elution of highly polar compounds in the strong solvent.

When the strong solvent, dichloromethane, was modified in the column by the addition of 10 vol% isopropanol, the additional peak was observed and recorded. Finally, the detector response returned to a value very close to its initial baseline at point 42, at which time data collecting was ceased.

The relationship of the variations in light-scattering response and UV oscillator strength with solvent type is as follows: the initial change in light scattering corresponds with the elution of saturated hydrocarbons and a small proportion of aromatic hydrocarbons. The saturated hydrocarbons cause the peak at point 33, and the decline in light scattering thereafter is indicative of the relatively complete elution of saturates and an associated contribution from eluted aromatics. The relatively abrupt rise in UV absorbance leading to point 37 is attributed to the elution of aromatic hydrocarbons in the weak solvent. Aromatic species having progressively increasing numbers of rings, as shown in part by the internal standard, continue to elute from the column with weak solvent. The steep rise in UV absorption which commences shortly after the start of the progressive change from weak to strong solvent and which culminates in the peak absorbance (point 39) after the composition of the moving phase has changed to strong solvent only is attributed to the elution of polar compounds. Polar compounds are eluted relatively rapidly and efficiently (having regard to their relatively high molecular weights and physico-chemical properties) by the strong solvent until they are substantially wholly removed from the column.

The elution of highly polar substances, evidenced by peaks 40 and 41, leads to complete recovery of the oil which was injected into the column.

During the succeeding 38 minutes while the stationary phase in the column is subjected to equilibration with weak solvent (i.e. from 26 minutes to 60 minutes from the instant of sample introduction), the initial properties of the stationary phase are regenerated and a second cycle of analysis can be implemented by injecting the next sample. Thus, the overall cycle time is 60 minutes. The overall cycle time may be reduced by increasing the flow rate of solvents through the column and/or by starting the introduction of the strong and modified strong solvents at earlier times.

The proportions of each hydrocarbon type or component in a sample are obtained by converting the light-scattering response to a linear function of total mass, and the UV oscillator strength to a function of the mass of aromatic carbon, as described herein, and integrating each over a retention time interval. Components are defined by retention time intervals. Thus, saturates may be defined, determined or considered as those compounds eluting in the range between 9 and 16 channels, single-ring aromatics as those compounds eluting in the range from 16 to 24 channels, 2-ring aromatics as those eluting at from 24 to 40 channels, 3-ring aromatics as those eluting at from 40 to 75 channels, 4-ring aromatics as those eluting at from 75 to 200 channels, weak polar components as those eluting at from 200 to 300 channels, and strong polar components as those eluting at from 300 to 400 channels. The use of the model compounds to define the components is described herein (e.g., with reference to FIG. 12).

The quality of a column is measured by chromatographing a "cocktail" containing toluene, anthracene, and coronene in cyclohexane. The column is run isocratically with cyclohexane and 0.01% 2-propanol. The capacity factors are 0.1, 0.5, and 2.0 for toluene, anthracene, and coronene, respectively, where the capacity factor is the quantity retention volume minus void volume divided by the void volume of the stationary packing phase in the column 11. Chromatography of this mixture is found to give a good indication of the quality of the column. If a column is contaminated with retained polars, or excessively aged, the capacity factors increase. It is also found that columns from different manufacturers display widely different capacity factor and separation performances, even though they are all nominally NH2 bonded silica. A summary of capacity factor data for different sources of adsorbent is given in Table 2. Columns with capacity factors for coronene greater than 5 gave poor separations due to low yields of aromatics and polar components.

TABLE 2

| Adsorbent | Capacity Factors, $R^1$ for $NH_2$ Functionalized Silicas | | |
|---|---|---|---|
| | Toluene | Anthracene | Coronene |
| Merck "Lichrosorb NH$_2$" | 0.1 | 0.5 | 2.0 |
| Merck "Lichrosorb NH$_2$" (aged)[2] | 0.1 | 0.6 | 4.3 |
| Merck "Lichroprep NH$_2$" | 0.1 | 0.7 | 2.7 |
| Dupont "Zorbax NH$_2$"[3] | 0.35 | 2.9 | >11 |
| Waters "Energy analysis Column" | 0.2 | 0.9 | 5.4 |

Notes:
[1] R equals $\frac{\text{Retention Volume} - \text{Void Volume}}{\text{Void Volume}}$
[2] Aged column was run with 50 cycles at semi-preparative scale loading (4 mg).
[3] Coronene elution required 40% strong solvent.

The separation achieved with cyclic semi-preparative scale use of this procedure shows good selectivity for micro-Conradson carbon residue (MCR), which is a measure of the coke forming tendency, and excellent selectivity for metallo-porphyrins.

In a practical test of the method as disclosed herein, Cold Lake bitumen was separated into 65% non-polars (saturates and aromatics) showing an MCR of 2.7 and 37% polars with an MCR of 34 wt%. The whole bitumen had a MCR of 14.3 wt%. Heavy Arabian Vacuum Resid was separated into a non-polar fraction of 53%–58% with an MCR of 9 and a polar fraction with yield of 43%–47% and an MCR of 45%–47%. The whole resid had an MCR of 23 wt%. There were no metalloporphyrins detectable by visible spectroscopy ($\leq 1$ ppm) in the non-polar fractions. These data indicate that the refractory components (i.e., materials which are considered to be detrimental to the quality of a hydrocarbon sample and/or which adversely affect its subsequent usage) are concentrated in the polars fraction and that a high yield, selective separation of nonpolars and polars has been achieved. The procedure retains aromatics as a function of their degree of conjugation. In all analyses using the method and equipment of the invention, 99+% of the saturates, aromatics, polar molecules and asphaltene fractions is recovered within a relatively short analysis cycle (e.g. 30 minutes). This contrasts with open column such as those used in pursuance of ASTM D-4003 prior methods in which sample recovery is incomplete, typically about 95% and wherein the analysis requires relatively large samples (e.g. of the order of 3 grams) and a relatively long sampling time (e.g. about 8 hours).

The regenerability of the stationary phase has been amply demonstrated in practical tests. Individual columns 11 have each been used for well over 100 analytical cycles with 4 mg loadings before any significant loss of performance has been observed. The chromatographic method and equipment herein described can readily be adapted to operate automatically. The complete analytical sequence as described by way of non-limitative example with reference to FIGS. 2 and 3 takes 30 minutes, although it can obviously take a different time, and within the overall time of each cycle, the operation of the pumps for the weak and strong solvents, the timing of the injection of the oil sample and the recording of UV absorption data (and mass detector data, if required) can all be controlled by automatic sequencing equipment. Since such automatic sequencing equipment is well known in the art and readily available from commercial manufacturers, and, moreover, since it does not form a direct part of the invention but only a conventional item of equipment, no description thereof will be furnished herein.

The chromatographic method and equipment herein described can be employed for the evaluation of a hydrocarbon mixture or in the regulation or optimization of processes for refining or upgrading a hydrocarbon feed, for example in the fractional distillation of hydrocarbon feeds, in the preparation of feeds for catalytic cracking wherein at least a portion of the feed is subjected to catalytic hydrogenation to reduce its refractory nature, and in solvent refining (e.g. deasphalting) of hydrocarbon mixtures, inter alia.

COMPARATIVE EXAMPLE

In the article in J. Chromatography (1981) 206, 289–300, C. Bollet et al. describe a high performance liquid chromatography (HPLC) technique that is said to be capable of analyzing a vacuum residue (boiling range above 535° C.) for saturates, aromatics, and polar compounds. The technique employs two procedures. In the first procedure, saturates are separated from aromatics and polars using a stationary phase of 10 micrometer silica bonded alkylamine in a column 20 cm. long by 4.8 mm. internal diameter. The mobile phase used was n-hexane, and it is stated that for asphaltene-containing samples, cyclohexane should be used as the mobile phase to avoid precipitation of asphaltenes. The article does not state that there is complete recovery of the sample in the eluent, but the article could be interpreted as implying that there is in fact 100% sample recovery.

Figure 4A:
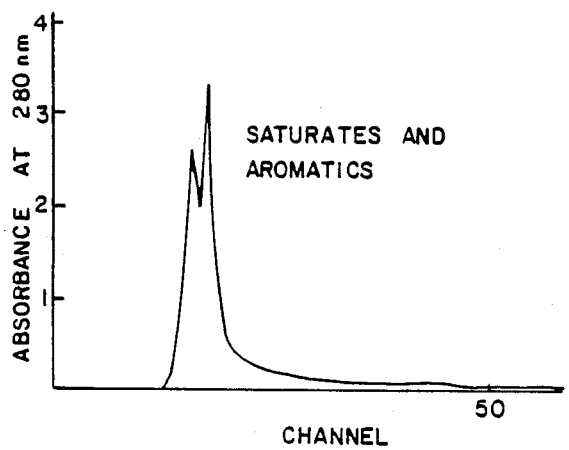
FIG. 4 shows in graphs (a), (b) and (c) absorbance versus time of eluents recovered during a repetition of the method described by Bollet et al in J. Chromatography (1981), 206 289–300.
Figure 4B:
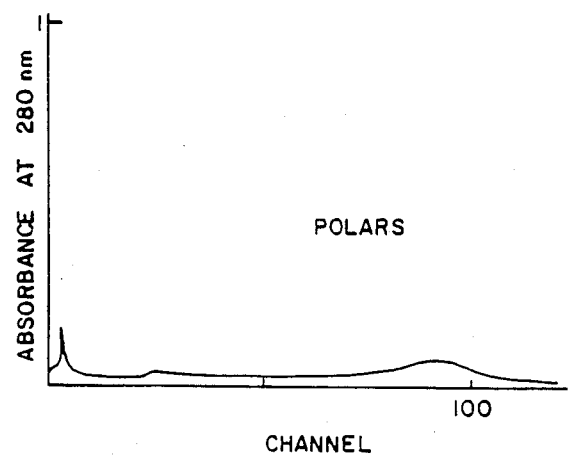

According to the second procedure of Bollet et al., in which separation of saturates together with aromatic compounds from polar compounds is carried out using a more polar solvent, a chromatographic column packed with Merck Lichrosorb-$NH_2$ functionalized silica was equilibrated with a solvent comprised of 85% cyclohexane and 15% chloroform at a flow rate of 2.0 ml/min. 120 microgram of an Arabian heavy vacuum distillation residue (950+° F., 510+° C.) was injected into the column in 20 microliter of cyclohexane solution. Detection was by monitoring UV absorbance at 254, 280, and 330 nm. The chromatogram generated (at 280 nm) is shown in FIG. 4a and indicates the dilution of saturates and aromatics. The flow was then reversed (backflush). Polar compounds eluted over the next 10 minutes by which time a stable baseline was reached. This is shown in FIG. 4B (UV absorbance monitored at 280 nm). A sharp peak as reported by Bollet et al. was not found. This completed the Bollet et al. analysis.

The method described by Bollet et al. was compared with the method disclosed herein and, as will be seen from the following results, the Bollet et al. method leaves a considerable amount of the sample material, principally polar compounds, in the column, whereas 100% recovery (or essentially 100% recovery) is achieved by the present method.

Figure 4C:
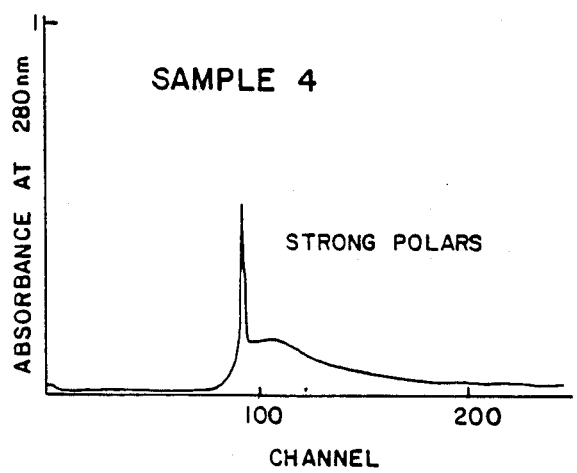

To show that polars recovery was incomplete, and as an example of one way of performing the method of the invention, the flow was reversed to its normal (forward) direction and a solvent of 90% dichloromethane and 10% isopropanol was introduced in a solvent gradient over 10 minutes. The absorbance was measured for 20 minutes during which time an additional peak due to strongly retained polars emerged at about 8 minutes (FIG. 4c, which shows the absorbance at 280 nm).

Thus, the Bollet et al. method leaves some of the polar material on the column. The absorbance in each of FIGS. 4a to 4c was integrated over time to obtain a measure of how much material was removed from the column in each step. The results are:

|  | Normalized Area (%) |
|---|---|
| Forward Flow Cyclohexane: Chloroform (85:15) Eluent: Saturates and Aromatics | 79.5 |
| Backflush Cyclohexane: Chloroform (85:15) Eluent: Polars | 8.4 |
| Forward Flow Dichloromethane: Isopropanol (90:10) Eluent: Additional Polars | 12.1 |

The amount of material which the Bollet et al. method leaves on the column is about 12% of the vacuum residue sample. This creates several problems which are avoided or overcome by the method disclosed herein, namely:

The material left on the column is not properly accounted for in the compositional analysis.

The material left on the column creates adsorbing sites for subsequent analysis, giving irreproducible results.

The material left on the column can eventually block the flow, causing high back pressure and loss of operation.

In order to achieve good recovery of residual oils from an HPLC column, the solid adsorbent material must be functionalized to shield the inorganic oxides and hydroxyls. The final eluting solvent must display solubility for asphaltenes and have a hydrogen bonding functionality and/or other highly polar functionality to neutralize the surface polarity of the adsorbent. The preferred combination is to use primary aminefunctionalized silica as the adsorbent and a mix of dichloromethane and isopropanol, where the isopropanol is present at volume concentrations in the range of from 1 to 50%, most preferably 10%, as the final solvent in the elution of the oil. This solvent may be introduced either in forward flow or backflush. It is the solubility and polarity aspects of the solvent which are important, not the flow direction.

In a modification of the separation, a three pump system is employed. The first pump delivers cyclohexane, the second dichloromethane, and the third isopropanol. The delivery rates are varied in time. Cyclohexane is used to elute saturates followed by aromatics, weakly polar compounds are then eluted with dichloromethane, and, finally, strongly polar molecules are eluted with 10% isopropanol in dichloromethane. The exact solvent composition program is not critical to obtaining information, since component assignments can be varied. It is important to increase the solubility parameter of the solvent as the chromatography proceeds, so that oil components of successively increasing solubility parameter can be desorbed and measured. Preferably, the solubility parameter of the solvent is increased progressively, rather than as a step change. However, a step change may be used and is within the scope of the present invention as defined by the appended claims.

The distinction of being able to accurately analyze residua is among the more important advantages which the method disclosed herein provides over the prior art. There are, however, several other advantages in the present method versus the prior art of Bollet et al., namely:

- Only a one-step procedure is used instead of two procedures, making the present method simpler.
- The aromatics are separated by their number of condensed aromatic rings, thus giving additional compositional information.
- A new detection scheme as described herein allows quantification of oil components without the need to obtain response factors for each compound type.

In each one of the refining or upgrading processes hereinbefore mentioned (i.e., distillation, solvent refining and catalytic cracking or coking), the present chromatographic method and equipment may be used to detect unacceptable levels of a particular type of hydrocarbon or other material, and upon such detection, a signal is derived or produced from which the operation of the process, and/or a step associated with the process, may be modulated in order to reduce the level of the undesirable hydrocarbon or other material to below the unacceptable level. Thus, referring to each of the said foregoing processes in turn, the following are the principal objectives and the manner in which they are achieved pursuant to the invention:

1. Distillation

In the distillation of hydrocarbon feeds containing asphaltenic material (hereinafter termed "asphaltenes" for brevity), a number of factors can lead to an excessive amount of entrainment or carryover of asphaltenes into the distillate fractions, particularly the gas oil fractions. Such factors include, but are not limited to, excessive stripping steam rates; excessively high heat input to the bottom recycle streams; excessively high feed rate.

Since the presence of excessive asphaltenes in a distillate is usually detrimental to the quality of the distillate and/or its subsequent use, the utilization of the equipment and method disclosed herein to detect excessive asphaltenes represents an important step forward in optimizing the operation of a distillation column.

According to this aspect, 0.4 mg samples of gas oil from the distillation column at a suitable standardized temperature (e.g. 25° C.) are injected via valve 13 into the equipment of FIG. 2 and subjected to the chromatographic analysis described with reference to FIGS. 2 and 3. The asphaltenes are highly polar and their concentration in the gas oil sample can readily be ascertained from the area beneath the UV oscillator strength curve during elution with the strong solvent (e.g. between points 38 and 42 of FIG. 3). The area beneath the UV oscillator strength curve is determined in accordance with any of the well known conventional techniques for so doing, and where the area is in excess of an acceptable area, any one or more of the known expedients to reduce asphaltene entrainment in the distillation tower may be implemented. Since it is not usually desirable to reduce the feed rate to the tower, the expedient which may be employed first is to reduce the rate of stripping steam. The reduction in heat input to the tower may be compensated for by increasing the temperature of the bottoms reflux temperature rather than the feed temperature to regulate asphaltenes carryover, as will be known to those skilled in this field. The regulation of the operation of the distillation tower in accordance with the asphaltenes as determined by the chromatographic method disclosed herein may be effected by manual adjustment, by operatives based on the output of the chromatograph, or automatically, also based on the output of the chromatograph.

2. Solvent Refining

In solvent refining, a feedstock is intimately contacted with a solvent having a selective solvency or affinity for a particular type of material in the feed and the resulting solution is separated from the remaining raffinate. In solvent deasphalting a feed containing asphaltenic materials, hereinafter termed asphaltenes for brevity, is mixed with a short chain n-paraffin, such as n-propane, which is completely miscible with non-asphaltenes but immiscible with asphaltenes whereby the latter form a second, heavier phase and can be removed by suitable separation techniques, e.g., decantation. If the deasphalting operation is performed at an excessively high rate for the separation of the asphaltene from the solvent-oil solution to occur in the available equipment, asphaltene will be entrained into the otherwise deasphalted solution.

In order to monitor the asphaltene content of the deasphalted solution, a sample of the latter is passed at a suitable standard temperature into chromatographic equipment of the type described with reference to FIG. 2, and the area under the UV oscillator strength curve during elution with strong solvent (corresponding to the area under curve 31 from points 38 to 40 in FIG. 3) is determined by any of the known techniques. If the area is in excess of the area representative of an acceptable amount of entrained asphaltenes, the feed rate is reduced either by manual intervention or automatically until an acceptable asphaltene entrainment level is attained.

3. Preparation of Catalytic Cracker Feeds (and/or Upgrading of Gas Oil)

Catalytic cracker feedstocks in particular, and gas oils in general, tend to contain proportions of molecules containing one or more aromatic rings and also polar molecules. The multi-aromatic molecules tend to resist cracking during their passage through a catalytic cracking unit and therefore tend to be concentrated in the cracked products, while polar molecules tend to decompose during cracking to give relatively large carbonaceous deposits on the catalyst, thereby impairing the catalytic activity of the latter. Moreover, gas oil and other fractions containing multi-ring aromatic structures tend to produce smoke on combustion, and, for at least the foregoing considerations, it is desirable to be able to control the levels of multi-aromatic molecules and polar molecules in gas oils and other hydrocarbon fractions.

One method by which the concentration of asphaltenes, resins and multi-aromatic ring molecules in a distillate fraction such as gas oil may be regulated is to control the cut-point of the fraction during distillation, and the method for doing this has already been described herein in relation to distillation. When the concentration of asphaltenes and multi-aromatic ring molecules in a distillate fraction from a distillation unit is found to be in excess of a desired maximum concentration using the chromatographic equipment and method as disclosed herein, signals representative of the UV-absorption characteristics of asphaltenes and multi-aromatic ring molecules and indicative of the excess concentrations thereof are derived and employed to control the operation of the distillation unit until the concentration of such molecules is reduced to an acceptable level in the distillate fraction.

In the context of catalytic cracking, one method of reducing the tendency of aromatic molecules (including multi-aromatic molecules) to be concentrated in the cracked products is to hydrogenate them since the resulting naphthenic structures (i.e. cycloparaffinic structures) crack relatively readily. Hydrogenation also tends to reduce the concentration of polar compounds. The hydrogenation is promoted by means of a suitable hydrogenation catalyst, e.g. a combination of metals from Groups VI and VII of the Periodic Table (e.g. Mo and Co) on a low-acid carrier such as alumina.

In relative terms, hydrogen is an expensive commodity and therefore it is highly desirable from the economics viewpoint to hydrogenate only that selected proportion of the hydrocarbon material whose hydrogenation will result in the production of cracked products of an acceptable quality. The proportion which is hydrogenated may be selected by diverting the desired proportion to a hydrogenating unit or passing all the feed through the hydrogenating unit and varying the hydrogenating conditions to effect the desired proportion of hydrogenation, or by a combination of both of the foregoing expedients in appropriate degrees. Generally speaking, the catalytic hydrotreatment of multi-aromatic molecules results in the hydrogenation of only one at a time of the aromatic rings in the molecules per hydrotreatment. The hydrogenated ring is cracked upon passage through the catalytic cracker and the resulting molecule with one less aromatic ring may be further hydrogenated to facilitate the cracking of an additional saturated aromatic ring upon each subsequent passage through the catalytic cracker until the content of refractory aromatic molecules in the cracked products is reduced to an acceptable level.

Catalytic hydrogenation of polar molecules is also practiced to the extent necessary to enhance the quality of the hydrocarbon fraction to a level suitable for its subsequent use, e.g. in catalytic cracking.

Figure 5:
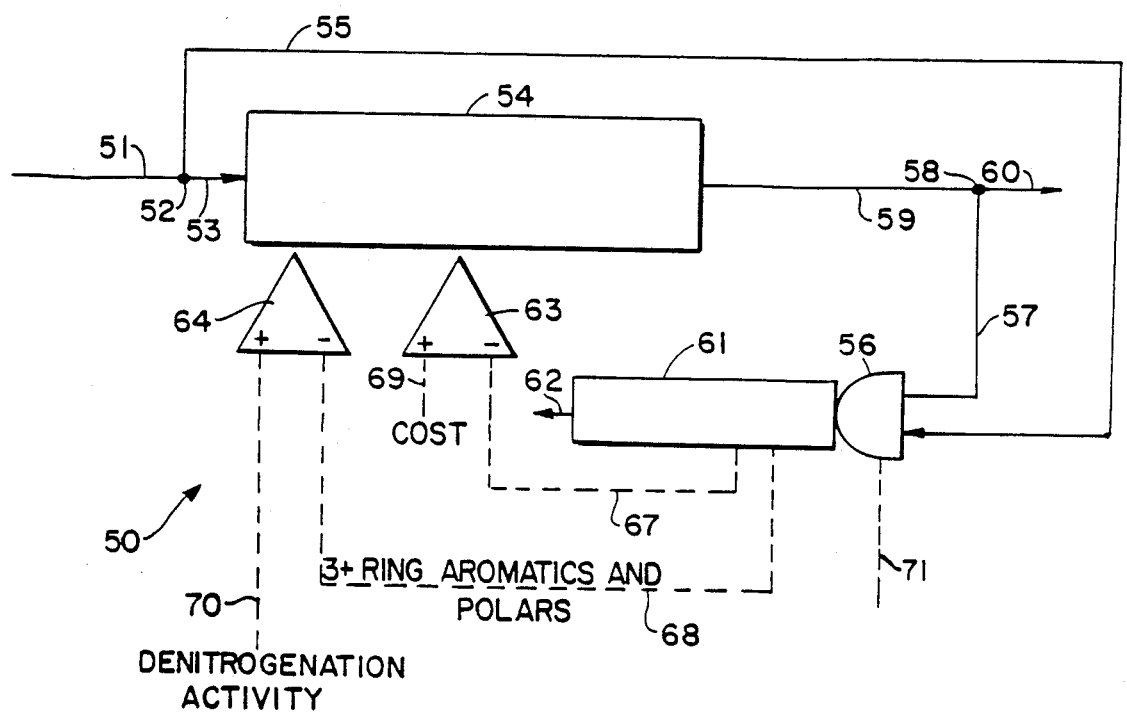
FIG. 5 is a chemical engineering flow sheet of a process and regulating equipment therefor, wherein the regulating equipment embodies apparatus for use according to one way of performing the method of the present invention.

By way of example, reference is now made to FIG. 5 which shows, in a block chemical engineering flow diagram, the principal features of a catalytic hydrotreatment unit 50 embodying process control. In this nonlimitative example, the unit is for enhancing the quality of a catalytic cracker feedstock, but it will be appreciated by those skilled in the art that it can be used to enhance the quality of feedstocks for other purposes.

The unprocessed feed (e.g. a gas oil fraction from a vacuum distillation tower) passes via line 51 to a sampling point 52 at which the main flow passes via line 53 to a catalytic hydrogenation facility, hereinafter termed "hydrotreater" 54 for brevity. Alternatively, product leaving the hydrotreater 54 via line 59, which passes to a catalytic cracking unit (not shown) via line 60, may be sampled via line 57 and valve 56.

An automatic high performance liquid chromatographic (HPLC) analyzing and control unit 16, embodying equipment of the type described herein with particular reference to FIG. 2, analyzes the samples of unprocessed feed from line 55 or processed feed from line 57, and regulates the operation of the hydrotreatment unit 50 so that the feed in line 60 has an acceptable quality. Used samples are discharged via line 62.

The HPLC unit 61 has a regulatory influence on at least the following (inter alia):

(a) the flow rate of feed through the
   hydrotreater and thereby the residence time or space velocity;

(b) the ratio of hydrogen to feed in the hydrotreater 54 as determined by a hydrogen control unit 63. As has already been stated herein, hydrogen is relatively expensive and an economic balance is preferably to be struck by comparing the cost of hydrogen usage with the increased value of hydrogenated feedstock. The hydrogen control unit 63 plays a part in achieving this economic balance.

(c) the operating temperatures of the hydrotreater 54 as determined by a temperature control unit 64. Higher operating temperatures increase the removal of heteroatoms (such as nitrogen) in polar molecules which tend to reduce the activity of the catalytic cracking unit while lower operating temperatures increase the saturation of aromatic rings in molecules containing them. An economic balance must be struck between the value of a processed feedstock of reduced polar molecule content and the value of the processed feedstock of lower saturated aromatic ring content. The temperature control unit 64 plays a part in achieving this overall balance.

The settings of each of the feed rate, the hydrogen control unit 63 and the temperature control unit 64 may each be adjusted by manual operation or by automatic operation or by a combination of manual and automatic operation. When automatic control of one or more settings is employed, the control may be by means of a computer (not shown)of conventional type. Suitable programs for a control computer to govern part or all of the operations of unit 50 can be devised by any competent programmer. Neither the control computer nor the software therefor will be described because both fall within the present state of the art and neither is directly germane to the present invention as defined by the appended claims.

The operation of the catalytic hydrotreatment unit 50 is now described with particular reference to preparing an upgraded catalytic cracker feedstock from a feed obtained from a vacuum distillation tower (not shown).

The raw feed in line 51 is initially passed, at least in a major proportion, via line 53 to the hydrotreater, and then via line 59 to the cat cracker feedline 60. Samples of the feed in line 55 and the product in line 57 are passed periodically (e.g. once every 60 minutes) and alternately to the HPLC unit 61 and therein analyzed for saturates, mono- and multi-aromatic ring-molecules and polar molecules (which latter will contain heteroatoms such as nitrogen and oxygen). The analysis by the HPLC unit 61 is effected in the manner herein described in general, and also in particular with reference to FIGS. 2 and 3. From the analysis in the unit 61, signals are derived in signal lines 67 and 68, representative of the composition of the raw feed.

Information on the feed may be used in a "feed-forward" control sense to set the best estimated conditions of flow rate, temperature and hydrogen pressure in the hydrotreater.

If the product in line 59 has an unacceptably high content of multi-ring aromatic molecules and polar molecules, the hydrogen control unit 63 operates to increase the partial pressure of hydrogen and the ratio of hydrogen to raw feed in the hydrotreater 54 subject to programmed cost constraint signals to the unit 63 provided from the control computer via signal line 69.

The normal setting of the temperature control unit 64 is that appropriate for the saturation of aromatic nuclei, i.e. a relatively low hydrotreating temperature within the range of from about 300 to 510° C. The normal setting, however, is subject to modulation by signals from the control computer which reach the temperature control unit 64 via signal line 70 to increase the hydrotreating temperature in order to reduce the heteroatom content (i.e. polar molecule content) of the raw feed to an acceptable level commensurate with an acceptable level of saturation of aromatic rings in the raw feed.

The setting of the valve 56 may be varied by human intervention or by a signal from the control computer (signal line 71) to the stream and frequency at which it is analyzed.

Some additional illustrations of the method disclosed herein are now given in the following non-limitative examples.

EXAMPLE 1

Production of Lube Basestock

The objective in producing lube basestock is to separate molecules from a feedstock which has good lubricating properties, principally including a high viscosity index. Saturated hydrocarbons and aromatics not exceeding one ring are most desirable. Two of the important steps in the production of a heavy lubestock of the type known as brightstock are: deasphalting a vacuum resid with propane to produce a deasphalted oil, and extraction of the condensed ring aromatics and resins from the deasphalted oil with a polar solvent such as phenol to produce a raffinate. The asphalt produced in the first step and the aromatics-rich extract produced in the second are byproducts which have other uses. HPLC techniques as described herein are used to monitor the molecular composition of each stream and to regulate the process conditions to achieve the highest yield of raffinate within quality specifications which are based on molecular composition.

Samples of each process stream were obtained and analyzed according to the description of FIGS. 2 and 3. The evaporative light scattering detector was employed. It was linearized according to equations (2) and (3) above by measuring its peak response to known concentrations of a vacuum gas oil. The integrated level of each component, whose retention time limits are defined by model components, is given in terms of weight percent of total sample in Table 3.

Observations of the data suggest process modifications which will be obvious to those skilled in production of lube basestock. The rejected asphalt stream from the deasphalting step contains 15.7% saturates. Some or all of these could be included in the deasphalted oil by lowering the temperature or increasing the treat ratio (i.e., the solvent to feedstock ratio) in the deasphalter. The deasphalted oil contains amounts of 3- and 4-ring aromatics which are below the detection limit but which are concentrated in the extract. The extraction step was effective at removing the 2-, 3- and 4-ring aromatics from the raffinate, but there is a trace amount of resins (polar compounds) remaining and some saturates were also removed. The selectivity of this separation could be improved by increasing the treat ratio, for example. It is assumed that process changes are made by balancing the cost of making the change versus the benefits in improved product quality or quantity.

TABLE 3

| | Molecular Composition of Lube Stocks (%) | | | | |
|---|---|---|---|---|---|
| | Resid | Asphalt | Deasphalted Oil | Extract | Raffinate |
| Saturates | 30.0 | 15.7 | 60.5 | 19.1 | 75.2 |
| Aromatics 1 | 19.4 | 14.6 | 28.8 | 34.5 | 22.6 |
| Aromatics 2 | 7.8 | 7.7 | 5.8 | 17.4 | 0.0 |
| Aromatics 3 | 2.9 | 5.7 | 0.0 | 10.1 | 0.0 |
| Aromatics 4 | 2.2 | 4.9 | 0.0 | 8.1 | 0.0 |
| Polars | 37.8 | 51.4 | 2.7 | 8.9 | 0.5 |

EXAMPLE 2.

Production of Cat Crackinq Feedstocks

A heavy vacuum gas oil and a heavy coker gas oil are produced by vacuum distillation and a fluid coking process, respectively. These streams are found to be too high in sulfur, nitrogen, 3+-ring aromatics, and polars for efficient cat cracking. They are, therefore, blended and subjected to a hydrotreating process wherein they are passed through two reactors in series. Both reactors are loaded with a commercial Co-Mo on alumina hydrotreating catalyst. The feed is comingled with hydrogen gas at a partial pressure of 1200 psi (8278 kPa) and the average bed temperature is 705° F. (373.9° C.). The residence time is about 22 min. in each reactor.

The molecular composition of the feed is compared to the product of the first reactor and the second series reactor by the HPLC method of the invention. The separation is effected by the method described with reference to FIGS. 2 and 3. The detector is a UV diode array spectrophotometer. The integrated oscillator strength is calculated as in equation (1) above and converted to weight percent of aromatic carbon by the correlation of FIG. 1. The composition of each stream is given in Table 4. It is apparent that the feedstock is upgraded across each reactor. The net upgrade results in a content of 3+-ring aromatics and polars which is only about half of the starting level. Both 1- and 2-ring aromatics are produced by hydrogenation of the polynuclear aromatics.

The information available in Table 4 may be used to regulate the process. If the product level of 3+-ring aromatics plus polars is below a set point determined to provide good cat cracker feedstock, the plant operator may decide either to decrease the residence time through both reactors or to bypass the second reactor altogether, for example. Other common means of control would be to vary hydrogen partial pressure or temperature or both.

TABLE 4

Molecular Compositions as Affected by Hydrotreating Upgrade (Units are Weight Percent Aromatic Carbon)

| Component | Feed | First Reactor Product | Second Reactor Product |
|---|---|---|---|
| 1-Ring Aromatic Core | 3.7 | 5.6 | 6.7 |
| 2-Ring Aromatic Core | 5.0 | 6.4 | 6.7 |
| 3-Ring Aromatic Core | 5.5 | 6.0 | 4.7 |
| 4-Ring Aromatic Core | 8.9 | 5.2 | 3.7 |
| Polar Core | 10.0 | 6.2 | 5.0 |

The invention defined by the appended claims is not confined to the specific embodiments herein disclosed. Moreover, any feature which is described in connection with one embodiment may be employed with any other embodiment without departing from the invention as defined by the appended claims. It is further remarked that the UV detection technique disclosed herein, deriving the integrated oscillator strength, may be used alone in HPLC for determining the level of aromatic carbon present or in combination with the mass sensitive measuring technique (using at least weak and strong eluting solvents) for measuring the level of saturates, aromatics and polars in the oil sample.

What is claimed is:

1. A method for the chromatographic analysis of hydrocarbon oil wherein at least 99% of the oil is eluted and analyzed, comprising the steps of:
    (a) passing a mixture of the hydrocarbon oil and a carrier phase in contact with a chromatographic stationary phase over a time interval so as to retain component of the hydrocarbon oil on said stationary phase;
    (B) passing in contact with the stationary phase a first mobile phase of a weak solvent having a solubility parameter ranging from 7.6 to 8.8 $cal^{0.5}cm^{-1.5}$ for a first time period at least during and after step (a) and recovering the weak solvent;
    (c) monitoring the weak solvent recovered in step (b) for a second time period comprising at least a time interval after the first time period and detecting eluent comprising aromatic hydrocarbons;
    (d) monitoring the weak solvent recovered in step (b) and detecting eluent comprising saturated hydrocarbons simultaneously with and after step (c);
    (e) passing in contact with the stationary phase a second mobile phase of a strong solvent having a solubility parameter ranging from 8.9 to 10.0 $cal^{0.5}cm^{-1.5}$ for a third time period which is at least after the second time period and recovering the strong solvent;
    (f) monitoring the strong solvent recovered in step (e) and detecting eluent comprising heteroatomic compounds, polar compounds, and asphalterric materials;
    (g) passing in contact with the stationary phase for a fourth time period which is at least after the third time period a third mobile phase of a material comprising the strong solvent and a hydrogen bonding solvent which is miscible therewith and recovering the material; and
    (h) monitoring the material recovered in step (g) and detecting eluent comprising moieties selected form the group consisting of polar compounds, asphaltives, and mixtures thereof.

2. The method of claim 1 wherein the hydrocarbon oil is free of asphaltives, the hydrogen bonding solvent is isopropanol, and the material monitored in step (h) comprises polar compounds.

3. The method of claim 1 wherein the hydrocarbon oil contains asphaltives, the hydrogen bonding solvent is isopropanol, and the material monitored in step (h) contains polars and asphaltives.

4. The method of claim 1 wherein the recovered mobile phases are irradiated with Uv light having a wave length range of which at least apart is within about 200 nm to about 400 nm over a sufficient time period that the recovered components in the mobile phases are subjected to irradiation, the mobile phases being substantially transparent to Uv light within the wave length range;
    monitoring the absorbance of the UV light by the irradiated components across the wave length range and deriving the integral of absorbance as a function of photon energy across the wave length range, and
    measuring the magnitude of the derived integral in at least one selected time interval corresponding with the elution of one or more components.

5. A method as claimed in claim 4, wherein molecules of toluene, anthracene and coronene are used for calibrating the stationary phase for 1-ring, 3-ring and 6-ring aromatics.

6. A method as claimed in claim 1, wherein absorbance of UV light by irradiated components is monitored using a diode array detector.

7. A method as claimed in claim 1, wherein the mobile phase is a solvent and wherein said method further comprises the further step (i) of detecting the total mass of components eluted from the stationary phase by a technique selected from: (1) determining the refractive index of the eluate; (2) solvent evaporation followed by flame ionization of the solvent-free eluate; and (3) solvent evaporation followed by monitoring of light-scattering of an aerosol of the solvent-free eluate.

* * * * *